(12) United States Patent
Martinez

(10) Patent No.: US 6,509,157 B1
(45) Date of Patent: Jan. 21, 2003

(54) 3 BLOCKED NUCLEIC ACID AMPLIFICATION PRIMERS

(75) Inventor: Tomás Ramon Martinez, Alamo, CA (US)

(73) Assignee: Roche Molecular Systems, Inc, Alameda, CA (US)

( * ) Notice: Subject to any disclaimer, the term of this patent is extended or adjusted under 35 U.S.C. 154(b) by 73 days.

(21) Appl. No.: 09/687,910

(22) Filed: Oct. 13, 2000

Related U.S. Application Data

(60) Provisional application No. 60/163,890, filed on Nov. 5, 1999.

(51) Int. Cl.⁷ ............................ C12Q 1/68; C12P 19/34; C07H 21/04
(52) U.S. Cl. .......................... 435/6; 435/91.2; 536/24.3
(58) Field of Search .................. 435/6, 91.2; 536/24.3

(56) References Cited

U.S. PATENT DOCUMENTS

| | | | |
|---|---|---|---|
| 4,973,679 A | * | 11/1990 | Caruthers et al. |
| 5,418,149 A | * | 5/1995 | Gelfand et al. |
| 5,635,347 A | * | 6/1997 | Link et al. ...................... 435/6 |
| 6,001,611 A | * | 12/1999 | Will ........................... 435/91.2 |

FOREIGN PATENT DOCUMENTS

| | | | |
|---|---|---|---|
| EP | 0 439 182 B1 | 4/1996 | |
| WO | WO-98/31830 A1 | * 7/1998 | ............ C12Q/1/68 |

OTHER PUBLICATIONS

Stratagene Catalog, p. 39, 1988.*
P. 20 of the 1997 Glen Research Product Catalog.

* cited by examiner

*Primary Examiner*—Jeffrey Fredman
*Assistant Examiner*—Christine Maupin
(74) *Attorney, Agent, or Firm*—Charles M. Doyle; George C. Jen; Pennie & Edmonds LLP

(57) ABSTRACT

The present invention provides reversibly blocked primers for use in the amplification of a nucleic acid sequence. Amplifications carried out using the blocked primers result in less non-specific amplification product, in particular, primer dimer, and a concomitant greater yield of the intended amplification product compared to amplifications carried out using unblocked primers.

8 Claims, No Drawings

3 BLOCKED NUCLEIC ACID AMPLIFICATION PRIMERS

This application claims priority under 35 U.S.C. §119(e) of provisional application Ser. No. 60/163,890, filed Nov. 5, 1999, incorporated herein by reference.

BACKGROUND OF THE INVENTION

1. Field of the Invention

The present invention relates to the field of molecular biology and nucleic acid chemistry. More specifically, it relates to methods and reagents for improving the yield of nucleic acid amplification reactions. The invention therefore has applications in any field in which nucleic acid amplification is used.

2. Description of Related Art

The invention of the polymerase chain reaction (PCR) made possible the in vitro amplification of nucleic acid sequences. PCR is described in U.S. Pat. Nos. 4,683,195; 4,683,202; and 4,965,188; Saiki et al., 1985, Science 230:1350–1354; Mullis et al., 1986, Cold Springs Harbor Symp. Quant. Biol. 51:263–273; and Mullis and Faloona, 1987, Methods Enzymol. 155:335–350; each of which is incorporated herein by reference. The development and application of PCR are described extensively in the literature. For example, a range of PCR—related topics are discussed in PCR Technology—principles and applications for DNA amplification, 1989, (ed. H. A. Erlich) Stockton Press, New York; PCR Protocols: A guide to methods and applications, 1990, (ed. M. A. Innis et al.) Academic Press, San Diego; and PCR Strategies, 1995, (ed. M. A. Innis et al.) Academic Press, San Diego; each of which is incorporated herein by reference. Commercial vendors, such as Perkin Elmer (Norwalk, Conn.), market PCR reagents and publish PCR protocols.

Since the original publication of nucleic acid amplification, various primer-based nucleic acid amplification methods have been described including, but not limited to, Ligase Chain Reaction (LCR, Wu and Wallace, 1989, Genomics 4:560–569 and Barany, 1991, Proc. Natl. Acad. Sci. USA 88:189–193); Polymerase Ligase Chain Reaction (Barany, 1991, PCR Methods and Applic. 1:5–16); Gap-LCR (PCT Patent Publication No. WO 90/01069); Repair Chain Reaction (European Patent Publication No. 439,182 A2); 3SR (Kwoh et al., 1989, Proc. Natl. Acad. Sci. USA 86:1173–1177; Guatelli et al., 1990, Proc. Natl. Acad. Sci. USA 87:1874–1878; PCT Patent Publication No. WO 92/08800); NASBA (U.S. Pat. No. 5,130,238); and strand displacement amplification (U.S. Pat. No. 5,455,166). All of the above references are incorporated herein by reference. A survey of amplification systems is provided in Abramson and Myers, 1993, Current Opinion in Biotechnology 4:41–47, incorporated herein by reference.

Specificity of primer-based amplification reactions largely depends on the specificity of primer hybridization. Under the elevated temperatures used in a typical amplification, the primers hybridize only to the intended target sequence. However, amplification reaction mixtures are typically assembled at room temperature, well below the temperature needed to insure primer hybridization specificity. Under such less stringent conditions, the primers may bind non-specifically to other only partially complementary nucleic acid sequences or to other primers and initiate the synthesis of undesired extension products, which can be amplified along with the target sequence. Amplification of non-specific primer extension products can compete with amplification of the desired target sequences and can significantly decrease the efficiency of the amplification of the desired sequence.

One frequently observed type of non-specific amplification product is a template independent artifact of amplification reactions referred to as "primer dimer". Primer dimer is a double-stranded fragment whose length typically is close to the sum of the two primer lengths and appears of occur when one primer is extended over the other primer. The resulting concatenation forms an undesired template which, because of its short length, is amplified efficiently.

Non-specific amplification can be reduced by reducing the formation of primer extension products prior to the start of the reaction. In one method, referred to as a "hot-start" protocol, one or more critical reagents are withheld from the reaction mixture until the temperature is raised sufficiently to provide the necessary hybridization specificity. In this manner, the reaction mixture cannot support primer extension during the time that the reaction conditions do not insure specific primer hybridization.

Manual hot-start methods, in which the reaction tubes are opened after the initial high temperature incubation step and the missing reagents are added, are labor intensive and increase the risk of contamination of the reaction mixture. Alternatively, a heat sensitive material, such as wax, can be used to separate or sequester reaction components, as described in U.S. Pat. No. 5,411,876, incorporated herein by reference, and Chou et al., 1992, Nucl. Acids Res. 20(7): 1717–1723, incorporated herein by reference. In these methods, a high temperature pre-reaction incubation melts the heat sensitive material, thereby allowing the reagents to mix.

Another method of reducing the formation of primer extension products prior to the start of the reaction relies on the heat-reversible inactivation of the DNA polymerase. U.S. Pat. Nos. 5,773,258 and 5,677,152, both incorporated herein by reference, describe DNA polymerases reversibly modified by the covalent attachment of a modifier group. Incubation of the inactivated DNA polymerase at high temperature results in cleavage of the modifier-enzyme bond, thereby releasing an active form of the enzyme.

Non-covalent reversible inhibition of a DNA polymerase by DNA polymerase-specific antibodies is described in U.S. Pat. Nos. 5,338,671, incorporated herein by reference.

Non-specific amplification also can be reduced by enzymatically degrading extension products formed prior to the start of the reaction using the methods described in U.S. Pat. No. 5,418,149, which is incorporated herein by reference. The degradation of newly-synthesized extension products is achieved by incorporating into the reaction mixture dUTP and UNG, and incubating the reaction mixture at 45–60° C. prior to carrying out the amplification reaction. Primer extension results in the formation of uracil-containing DNA, which is degraded by UNG under the pre-amplification conditions. A disadvantage of this method is that the degradation of extension product competes with the formation of extension product and the elimination of non-specific primer extension product is likely to be less complete. An advantage of this method is that uracil-containing DNA introduced into the reaction mixture as a contamination from a previous reaction is also degraded and, thus, the method also reduces the problem of contamination of a PCR by the amplified nucleic acid from previous reactions.

Conventional techniques of molecular biology and nucleic acid chemistry, which are within the skill of the art, are fully explained fully in the literature. See, for example, Sambrook et al., 1989, Molecular Cloning—A Laboratory Manual, Cold Spring Harbor Laboratory, Cold Spring Harbor, New York; Oligonucleotide Synthesis (M. J. Gait, ed., 1984); Nucleic Acid Hybridization (B. D. Hames and S. J. Higgins. eds., 1984); and a series, Methods in Enzymology (Academic Press, Inc.), all of which are incorporated herein by reference. All patents, patent applications, and publications mentioned herein, both supra and infra, are incorporated herein by reference.

SUMMARY OF THE INVENTION

The present invention provides methods and reagents for the in vitro amplification of a nucleic acid sequence using a primer-based amplification reaction which provide a simple and economical solution to the problem of non-specific amplification. The methods use oligonucleotide primers reversibly blocked at the 3'-hydroxy terminus which can be unblocked by incubation in the amplification reaction mixture at an elevated temperature. Non-specific amplification is reduced because the reaction mixture does not support primer extension until the temperature of the reaction mixture has been elevated to a temperature which insures primer hybridization specificity.

One aspect of the invention relates to kits for the in vitro amplification of a nucleic acid sequence using a primer-based amplification reaction, which comprise at least one reversibly blocked primer, preferably two, for each intended target. A kit typically will comprise one or more amplification reagents, e.g., a nucleic acid polymerase or ligase, nucleoside triphosphates, or suitable buffers.

Another aspect of the present invention relates to methods for amplifying a nucleic acid which comprise carrying out a primer-based nucleic acid amplification reaction using at least one reversibly-blocked primer.

In a preferred embodiment, the present invention provides a method for the amplification of a target nucleic acid contained in a sample, comprising:

(a) contacting the sample with an amplification reaction mixture containing a reversibly blocked amplification primer; and (b) incubating the resulting mixture of step (a) at a temperature which is greater than about 50° C. for a time sufficient to deblock the primer and allow formation of primer extension products.

In some embodiments of the invention, the incubation step, step (b), is carried out prior to the start of the amplification reaction. In other embodiments, the incubation which results in deblocking of the primer is an integral step in the amplification process. For example, the high-temperature denaturation step carried out in each cycle of a polymerase chain reaction (PCR) amplification can function simultaneously to deblock the primer.

In a preferred embodiment of the invention, the amplification reaction is a polymerase chain reaction (PCR) wherein at least one and, preferably all, of the primers are reversibly blocked. An initial incubation of the reaction mixture carried out at a temperature which is higher than the annealing temperature of the amplification reaction results in the deblocking of the primers (or fraction of the primers— deblocking need not be 100%). Because the primers are incapable of being extended until the temperature is above the temperature which insures specificity of the amplification reaction, non-specific amplification is reduced.

Another aspect of the invention relates to amplification reaction mixtures which contain at least one reversibly blocked primer along with reagents for carrying out the amplification reaction. In a preferred embodiment, the amplification reaction mixture contains a pair of reversibly blocked oligonucleotide primers for carrying out a PCR.

DETAILED DESCRIPTION OF THE INVENTION

To aid in understanding the invention, several terms are defined below.

The terms "nucleic acid" and "oligonucleotide" refer to polydeoxyribonucleotides (containing 2-deoxy-D-ribose), to polyribonucleotides (containing D-ribose), and to any other type of polynucleotide which is an N glycoside of a purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise non-purine or non-pyrimidine nucleotide analogs.

Oligonucleotides can be prepared by any suitable method, including direct chemical synthesis by a method such as the phosphotriester method of Narang et al., 1979, *Meth. Enzymol.* 68:90–99; the phosphodiester method of Brown et al., 1979, *Meth. Enzymol.* 68:109–151; the diethylphosphoramidite method of Beaucage et al., 1981, *Tetrahedron Lett.* 22:1859–1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165–187, incorporated herein by reference.

The term "primer" refers to an oligonucleotide capable of acting as a point of initiation of DNA synthesis under conditions in which synthesis of a primer extension product complementary to a nucleic acid strand is induced, i.e., either in the presence of four different nucleoside triphosphates and an agent for extension (e.g., a DNA polymerase or reverse transcriptase) in an appropriate buffer and at a suitable temperature. As used herein, the term "primer" is intended to encompass the oligonucleotides used in ligation-mediated amplification processes, in which one oligonucleotide is "extended" by ligation to a second oligonucleotide which hybridizes at an adjacent position. Thus, the term "primer extension", as used herein, refers to both the polymerization of individual nucleoside triphosphates using the primer as a point of initiation of DNA synthesis and to the ligation of two oligonucleotides to form an extended product.

A primer is preferably a single-stranded DNA. The appropriate length of a primer depends on the intended use of the primer but typically ranges from 6 to 50 nucleotides, preferably from 15–35 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning of the amplified product. The region of the primer which is sufficiently complementary to the template to hybridize is referred to herein as the hybridizing region.

The terms "target, "target sequence", "target region", and "target nucleic acid" refer to a region or subsequence of a nucleic acid which is to be amplified.

The term "hybridization" refers the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which only fully complementary nucleic acid strands will hybridize are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair concentration of the oligonucleotides, ionic strength, and incidence of mismatched base pairs, following the guidance provided by the art (see, e.g., Sambrook et al., 1989, *Molecular Cloning—A Laboratory Manual*, Cold Spring Harbor Laboratory, Cold Spring Harbor, New York; and Wetmur; 1991, Critical Review in Biochem. and Mol. Biol. 26(3/4):227–259; both incorporated herein by reference).

As used herein, a primer is "specific" for a target sequence if, when used in an amplification reaction under sufficiently stringent conditions, the primer hybridizes primarily only to the target nucleic acid. Typically, a primer is specific for a target sequence if the primer-target duplex stability is greater than the stability of a duplex formed between the primer and any other sequence found in the sample. One of skill in the art will recognize that various factors, such as base composition of the primer and the location of the mismatches, will affect the specificity of the primer, and that routine experimental confirmation of the primer specificity will be needed in most cases. Hybridization conditions can be chosen under which the primer can form stable duplexes only with a target sequence. Thus, the use of target-specific primers under suitably stringent amplification conditions enables the specific amplification of those target sequences which contain the target primer binding sites. The use of sequence-specific amplification conditions enables the specific amplification of those target sequences which contain the exactly complementary primer binding sites.

The term "non-specific amplification" refers to the amplification of nucleic acid sequences other than the target sequence which results from primers hybridizing to sequences other than the target sequence and then serving as a substrate for primer extension. The hybridization of a primer to a non-target sequence is referred to as "non-specific hybridization" and can occur during the lower temperature, reduced stringency, pre-amplification conditions.

The term "primer dimer" refers to template-independent non-specific amplification product, which is believed to result from primer extensions wherein another primer serves as a template. Although primer dimer frequently appears to be a concatamer of two primers, i.e., a dimer, concatamers of more than two primers also occur. The term "primer dimer" is used herein generically to encompasses template-independent non-specific amplification product.

The term "reaction mixture" refers to a solution containing reagents necessary to carry out a given reaction. An "amplification reaction mixture", which refers to a solution containing reagents necessary to carry out an amplification reaction, typically contains oligonucleotide primers and a DNA polymerase or ligase in a suitable buffer. A "PCR reaction mixture" typically contains oligonucleotide primers, a DNA polymerase (most typically a thermostable DNA polymerase), dNTP's, and a divalent metal cation in a suitable buffer. A reaction mixture is referred to as complete if it contains all reagents necessary to enable the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction components which includes the blocked primers of the invention.

All patents, patent applications, and publications cited herein, both supra and infra, are incorporated herein by reference.

Reversibly Blocked Primers

A primer oligonucleotide typically is between about 5 and about 50 nucleotides in length, preferably between about 15 and about 35 nucleotides in length. Typically, primers consist of four conventional (also referred to as major) deoxyribonucleotides of DNA contain the purine bases adenine and guanine and the pyrimidine bases cytosine and thymine. The present invention is not limited to primers consisting only of conventional nucleotides. Any nucleotide analog which can be used in an amplification primer is useable in the present invention. Examples of unconventional nucleotides include 3-methyladenine, 7-methylguanine, 3-methylguanine, 5-methyl cytosine, and 5-hydroxymethyl cytosine.

The amplification primers of the invention are reversibly blocked by the covalent attachment of a blocking group to the 3'-hydroxy terminus of the primer. Reversible blocking groups suitable for use in the primers of the present invention include triyarylmethyl groups represented by the formula:

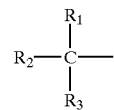

wherein $R_1$, $R_2$, and $R_3$ represent independently an aryl group, such a phenyl, napthyl, quinolyl, flryhienyl, or other nitrogen, sulfuir, and/or oxygen-containing heterocyclic ring; or such aryl groups with a monosubstituent such as halide (F, Cl, Br, or I), nitro, lower alkyl, lower alkoxy, lower alkyl, and aryl, aralkyl, and cycloalkyl containing up to 10 carbon atoms. $R_2$ and $R_3$ each also may be alkyl, aralkyl, or cycloalkyl containing up to 10 carbon atoms. Preferably, the reversible blocking group is a dimethoxytrityl group.

U.S. Pat. No. 4,973,679, incorporated herein by reference, describes a wide variety of triarylmethyl groups for use in DNA synthesis. Each of these groups may be suitable for use in the present methods depending on the stability of the blocked oligonucleotide, which is routinely determined as described herein.

One of skill in the art will recognize that, in general, the blocking groups described above vary in their stability, i.e., the time and conditions required to remove the group. More or less stable blocking groups may be desired depending on the application. Empirical selection of a reversible blocking group with the desired stability from the class of compounds described can be carried out routinely by one of skill in the art following the guidance provided herein. Preferably, suitability of a particular group is determined empirically by using the reversibly blocked primers in an amplification reaction. Successfuil amplification indicates that the blocking group is removable under the reaction conditions used.

The use of blocked primers prevents extension of any primer during the low-temperature, pre-amplification set-up stage. The blocking group is removed, thereby allowing primer extension, only after the reaction temperature has been raised to a temperature which insures reaction specificity. Thus, use of the reversibly blocked primers provides a "hot-start" amplification.

Synthesis of Blocked Primers

Synthesis of the blocked primers is carried out using standard chemical means well known in the art, for example, the diethylphosphoramidite method of Beaucage et al., 1981, Tetrahedron Lett. 22:1859–1862; and the solid support method of U.S. Pat. No. 4,458,066, each incorporated herein by reference.

In the solid support method, an initial nucleotide is coupled to the solid support, typically a derivatized controlled pore glass (CPG). The oligonucleotide is extended by the sequential addition of nucleotides until the desired sequence is obtained. The sequential extension involves the following steps:
1. removing a protecting group from the partially synthesized, support-bound oligonucleotide chain to generate a reactive hydroxyl group;
2. coupling a nucleotide to the support-bound oligonucleotide chain through a phosphite linkage;
3. capping unreacted hydroxyl groups on any support-bound oligonucleotides not extended; and
4. oxidizing the phosphite linkage to yield a phosphate linkage.

The above cycles are repeated until the desired oligonucleotide is synthesized.

Typically, following the last extention step, the protecting group attached to the last nucleotide added is removed, the oligonucleotide is cleaved from the solid support under basic conditions, and the resulting oligonucleotide is purified by standard methods, such as HPLC purification. Alternatively, the final protecting group can used to facilitate purification and removed following purification.

Although DNA synthesis can be carried out in either direction, synthesis generally is carried out in the 3' to 5' direction by adding nucleotides to the 5' end of the growing chain. Synthesis in this direction is carried out using nucleotide phosphoramidites in which the phosphoramidite group is attached to the 3'-oxygen and a protecting group, typically a dimethoxytrityl (DMT) group, attached to the 5'-oxygen. When synthesized in this direction, the product obtained prior to removal of the final protecting group is an oligonucleotide with a protecting group attached to the 5' terminus.

Alternatively, DNA synthesis can be carried out in the 5' to 3' direction by adding nucleotides to the 3' end of the growing chain. Synthesis in this direction is carried out using nucleotide phosphoramidites in which the phosphoramidite group is attached to the 5'-oxygen and a protecting group, again typically a dimethoxytrityl group, is attached to the 3'-oxygen. When synthesized in this direction, the product obtained prior to removal of the final protecting group is an oligonucleotide with a protecting group attached to the 3' terminus.

Synthesis in the 5' to 3' direction provides a convenient method of synthesizing an oligonucleotide with a blocking group attached to the 3' terminal oxygen. Omission of a deprotection step following addition of the final nucleotide to the oligonucleotide chain resulting in the synthesis of an oligonucleotide with a protecting (i.e., blocking) group attached to the 3' terminal oxygen.

Preferably, the synthesis reaction is carried out in a commercially available automatic DNA synthesizer (e.g., ABI 374 DNA synthesizer from Perkin Elmer, Applied Biosystems Division, Foster City, Calif.) using commercially available nucleotide phosphoramidites (e.g., from Perkin Elmer, Norwalk, Conn.). Nucleotide phosphoramidites usable for synthesis in the 5' to 3' direction, which contain a dimethoxytrityl group attached to the 3' oxygen, are commercially available from Perkin Elmer or Glenn Research (Sterling, Va.).

As noted above, it is known in the art that the final dimethoxytrityl protecting group can be used to facilitate purification. However, the protecting group always has been removed prior to use in an amplification reaction. In the present invention, the final protecting group, or a group substituted for the protecting group, is used as a reversible blocking group in an amplification reaction.

In a preferred embodiment, reversibly blocked primers are synthesized in the 5' to 3' direction using commercially available phosphoramidites with a dimethoxytrityl (DMT) protecting group attached to the 3' oxygen. The final deprotecting step is omitted, resulting in oligonucleotides with DMT groups remaining on the 3' terminus. Primers reversibly blocked with other triarylmethyl groups are synthesized in the same manner, but with a nucleotide phosphoramidites containing the desired blocking group added in the final extension step.

Alternatively, a blocking group can be added to an oligonucleotide following the final deprotecting step, which removes the final 3' DMT. The fully synthesized oligonucleotide, prior to being cleaved from the CPG, is reacted with a synthesized a triarylmethyl halide, such as a chloride or bromine. Reddy et al., 1987, Tetrahedron Letters 28(1):23–26, incorporated herein by reference, describe rapid and efficient methods for the tritylation of a oligonucleotide bound to a CPG, which are usefuil for synthesizing the 3' tritylated oligonucleotides of the present invention. Useful modifications to the methods described therein include providing the tetra-n-butylammonium in the form of a chloride salt and using 2,6,-Lutidine in place of the 2,4,6-collidine.

The synthesis of exemplary reversibly blocked primers is described in the examples. Additional reversibly blocked primers can be synthesized using standard synthesis methods in an analogous manner.

Amplifications using Reversibly Blocked Primers

The methods of the present invention comprise carrying out a primer-based amplification using the reversibly blocked primers of the present invention. In general, the reversibly blocked primers can be substituted for unblocked primers containing the same nucleotide sequence in a primer-based amplification with no change in the amplification reaction conditions. Of course, one of skill in the art will recognize that routine minor re-optimization of the reaction conditions may be beneficial in most reactions.

In a preferred embodiment, the reversibly blocked primers of the present invention are used in the polymerase chain reaction (PCR). However, the invention is not restricted to any particular amplification system. The reversibly blocked primers of the present invention can be used in any primer-based amplification system in which primer dimer or non-specific amplification product can be formed. Examples include the amplification methods described in the references cited above. As other systems are developed, those systems may benefit by practice of this invention.

In a typical PCR, which is carried out using thermostable enzymes, the high temperature denaturation step also can serve to remove the blocking groups from the primers, although it may be desirable to lengthen the initial high temperature step to facilitate more complete de-blocking of the primers. In isothermal amlification method, such as NASBA or TMA, which can be carried out using non-thermostable enzymes, the reaction conditions may not be sufficient to remove the blocking groups. In this case, a pre-reaction incubation is used to de-block the primers. It will be clear to one of skill in the art that any needed non-thermostable enzymes would be added to the reaction mixture subsequent to the high temperature de-blocking step.

The present invention is compatible with other methods of reducing non-specific amplification. For example, the present invention can be used in an amplification carried out using a reversibly inactivated enzyme as described in U.S. Pat. Nos. 5,677,152, and 5,773,258, each incorporated herein by reference. The use of a reversibly inactivated enzyme, which is re-activated under the high temperature reaction conditions, further reduces non-specific amplification by inhibiting primer extension of any deblocked primers prior to the start of the reaction. A reversibly inactivated thermostable DNA polymerase, developed and manufactured by Hoffmann-La Roche (Nutley, N.J.) and marketed by Perkin Elmer (Norwalk, Conn.), is described in Birch et al., 1996, Nature 381(6581):445–446, incorporated herein by reference.

The present invention also can be used in conjunction with the modified primers described in European Patent application No. 0 866,071 and co-pending U.S. application Ser. No. 09/039,866, both incorporated herein by reference. As described therein, primers can be modified by the covalent attachment of a modifier group to the exocyclic amine of a nucleotide at or near the 3' terminus. The attachment of a group to the exocyclic amine does not interfere with the attachment of a blocking group to the 3' terminal hydroxyl group, as specified herein.

Sample preparation methods suitable for amplification reactions are well known in the art and fully described in the literature cited herein. The particular method used is not a critical part of the present invention. One of skill in the art can optimize reaction conditions for use with the known sample preparation methods.

Methods of analyzing amplified nucleic acid are well known in the art and fully described in the literature cited herein. The particular method used is not a critical part of the present invention. One of skill in the art can select a suitable analysis method depending on the application.

A preferred method for analyzing an amplification reaction is by monitoring the increase in the total amount of double-stranded DNA in the reaction mixture, as described in Higuchi et al., 1992, Bio/Technology 10:413–417; Higuchi et al., 1993, Bio/Technology 11:1026–1030; European Patent Publication No. 512,334; and copending U.S. Pat. application Ser. No. 08/266,061; each incorporated herein by reference. In this method, referred to herein as "kinetic PCR", the detection of double-stranded DNA relies on the increased fluorescence that ethidium bromide (EtBr) and other DNA binding labels exhibit when bound to double-stranded DNA. The amplification is carried out in the presence of the label. The increase of double-stranded DNA resulting from the synthesis of target sequences results in a detectable increase in fluorescence, which is monitored during the amplification. Thus, the methods enable monitoring the progress of an amplification reaction.

In a kinetic PCR, the measured fluorescence depends on the total amount of double-stranded DNA present, whether resulting from non-specific amplification or from amplification of the target sequence. Monitoring the fluorescence allows measurement of the increase in the total amount of double-stranded DNA is measured, but the increase resulting from amplification of the target sequence is not measured independently from the increase resulting from non-specific amplification product. The blocked primers of the present invention are particularly useful in kinetic PCR because they not only reduce the amount of primer dimer formed, but also delay the formation of detectable amounts of primer dimer. A delay of primer dimer formation until after a significant increase in target sequence has occurred enables independent monitoring of the amplification of target sequences and minimizes the interference from primer dimer.

Kits

The present invention also relates to kits, typically multi-container units comprising useful components for practicing the present method. A useful kit contains primers, at least one of which is blocked as described herein, for nucleic acid amplification. Other optional components of the kit include, for example, an agent to catalyze the synthesis of primer extension products, the substrate nucleoside triphosphates, appropriate reaction buffers, and instructions for carrying out the present method.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

Synthesis of DMT-blocked Primers

Primers blocked with a dimethoxytrityl group attached to the 3' terminal oxygen were synthesized in the 5' to 3' direction on an ABI 394 DNA synthesizer (Perkin Elmer, Applied Biosystems Division, Foster City, Calif.). The CPG and nucleotide phosphoramidites were obtained from Glenn Research (Sterling, Va.). Conventional synthesis conditions were used, essentially as recommended by the manufacturers.

The crude DMT-DNA was purified by standard DMT On/Off HPLC using a Rainin Pure-DNA column on a Rainin HPLC system (Rainin Instrument Co, Woburn, Mass.), except that the DMT was not removed following purification. The oligonucleotides were analyzed using a ABI capillary electrophoresis system (Perkin Elmer, Applied Biosystems Division, Foster City, Calif.) or by denaturing anion-exchange HPLC chromatography on a Dionex Nucleopak column (Dionex Corp, Sunnyvale, Calif.).

EXAMPLE 2

Synthesis of Reversibly Blocked Primers

Primers blocked with other groups attached to the 3' terminal hydroxy are synthesized by reacting a CPG-bound oligonucleotide with an active halide of the desired triaryl methyl group, essentially as described above and in Reddy et al., 1987, supra.

An oligonucleotide primer with the desired sequence is synthesized in the 5' to 3' direction as in example 1, except that the final DMT group is removed. Prior to cleavage of the oligonucleotide from the CPG support, the oligonucleotide is treated with an equimolar (0.5 M) solution of tetra-n-butylammonium salts (Cl, $ClO_4$, or $NO_3$) and the active halide in methylene chloride containing 2,4,6-collidine or 2,6-lutidine (1.5 eq.) for 15 to 30 minutes. The reaction is quenched by passing an excess amount of methylene chloride through the CPG column. The modified oligonucleotide is then cleaved from the CPG and purified as usual.

EXAMPLE 3

Amplifications using Reversibly Blocked Primers

To demonstrate the effect of the blocked primers on the formation of primer dimer, comparisons were carried out of amplifications of HIV-1 DNA using both blocked and unblocked primers.

Target Nucleic Acid

Plasmids containing a segment of HIV-1 subtype O DNA from the gag gene were used as a target.

Primers

Amplifications were carried out using both unblocked and blocked primers. The nucleotide sequences of the unblocked primers are shown below, oriented in the 5' to 3' direction. These primers amplify a portion of the gag gene from an HIV-O sequence.

| | HIV-1 Amplification Primers | |
|---|---|---|
| Primer | Seq. ID No. | Sequence |
| Upstream | | |
| KY723 | (SEQ ID NO: 1) | GCATGGGTAAAGGCAGTAGAAGA |
| WL723 | (SEQ ID NO: 2) | GCATGGGTAAAGGCAGTAGAA |
| Downstream (RT) | | |
| GAG022 | (SEQ ID NO: 3) | CCAGCAATGTCACTTCCTGTTGG |
| WL022 | (SEQ ID NO: 4) | CCAGCAATGTCACTTCCTGTTG |

Primers WL723 (SEQ ID NO: 2) and WL022 (SEQ ID NO: 4) were synthesized to have a DMT group attached to the 3' terminus and are referred to as "blocked" primers in the results section, below. Primers KY723 (SEQ ID NO: 1) and GAG022 (SEQ ID NO: 3) were synthesized to contain a free 3' OH group and are referred to as "unblocked" primers in the results section, below.

Amplification

Amplifications were carried out in 100 µl reactions volumes containing the following reagents:

>$10^9$ copies of HIV template DNA,
0.3 µM of each primer (30 pmoles)
50 mM Tricine (pH 8.0),
135 mM KOAc,
300 µM each dATP, dCTP, and dGTP,
600 µM dUTP,
3 mM MnOAc,
12.5% Glycerol.
50 units of Z05 DNA polymerase*,
10 units of UNG**, and
0.5 µg/ml ethidium bromide.

* described in U.S. Pat. No. 5,455,170
** manufactured and developed by Hoffmann-La Roche and marketed by Perkin Elmer, Norwalk, Conn.

Thermal cycling of each reaction was carried out in a GeneAmp PCR system 9600 thermal cycler (Perkin Elmer, Norwalk, Conn.) using the following temperature profile:

| | |
|---|---|
| Pre-reaction incubation | 45° C. for 7 minutes |
| | 50° C. for 5 minutes |
| Reactivation incubation | 97° C. for 10 minutes |
| 60 cycles: | denature at 97° C. for 60 seconds, |
| | anneal/extend at 55.5° C. for 60 seconds |

The pre-reaction incubation is to allow the UNG to degrade any primer extension products formed during the low temperature reaction setup, as described in U.S. Pat. No. 5,418,149, incorporated herein by reference. The reactivation incubation results in the removal of the blocking DMT groups from a significant fraction of the primers. The denaturation incubation during each cycle results in deblocking of a portion of the remaining blocked primers.

Detection of Amplified Product

The accumulation of amplified product was measured at each cycle during the reaction using the kinetic PCR methods described above. The fluorescence of the ethidium bromide in the reaction mixture, which fluoresces more strongly when intercalated into double-stranded DNA, was monitored to measure the increase in double-stranded DNA during amplification. Reactions were monitored by measuring the fluorescence of the reaction mixture as described in copending U.S. patent application Ser. No. 08/266,061, incorporated herein by reference.

Because the kinetic PCR methods only measure an increase in the total amount of double-stranded DNA, non-specific amplification product is not measured independently of the intended amplification product. In order to measure the occurrence of template-independent non-specific amplification products (primer-dimer), additional reactions were carried out without template nucleic acid. In such template-free reactions, any increase in double-stranded DNA is attributable to the formation of template-independent non-specific amplification product.

Fluorescence measurements were normalized by dividing by an initial fluorescence measurement obtained during a cycle early in the reaction while the fluorescence measurements between cycles were relatively constant. The cycle number chosen for the initial fluorescence measurement was the same for all reactions compared, so that all measurements represent increases relative to the same reaction cycle. Reaction fluorescence in target-free reactions remained relatively constant until primer dimer formed. In most reactions, if enough amplification cycles are carried out, primer dimer eventually becomes detectable. The effect of the blocked primers can be seen from a comparison of the number of cycles carried out until primer dimer is formed, if at all.

To quantify the differences among the reactions, the results were expressed in terms of the number of amplification cycles carried out until the fluorescence exceeded an arbitrary fluorescence level (AFL). The AFL was chosen close to the baseline fluorescence level, but above the range of random fluctuations in the measured fluorescence, so that the reaction kinetics were measured during the geometric growth phase of the amplification. Accumulation of amplified product in later cycles inhibits the reaction and eventually leads to a reaction plateau.

Results

The results comparing reactions using unblocked and blocked primers are provided in the table, below An AFL of 1.2 was chosen for all reactions, and the results are reported as the number of cycles until the fluorescence reached the AFL. Because the reaction consists of discrete cycles, the fluorescence typically increases from below the AFL to above the AFL in a single cycle. The time to reach the AFL was calculated by interpolating the fluorescence measurements between cycles, which resulted in a value reported as a fraction of the cycle. Results for amplifications carried out with target template represents an average of two replicate amplifications. Results for amplifications carried out without target template represents an average of eight replicate amplifications. PATENT

| | | Cycles to reach AFL | | |
|---|---|---|---|---|
| | Upstream Primer | Downstream Primer | Viral DNA template | Neg. Control |
| A | unblocked | unblocked | 8 | 36.2 |
| B | blocked | unblocked | 9.8 | 50 |
| C | unblocked | blocked | 10.8 | 41.2 |
| D | blocked | blocked | 13.7 | 54 |

The data indicate that the reversibly-blocked primers apparently delay the amplification of target nucleic acid such that the AFL is reached several cycles later. The delay did not correspond to a reduction in the final yield of specific amplification product (data not shown). All amplifications of target nucleic acid were observed to reach a plateau within the 60 cycles used in the experiment.

The data indicate that the delay in the formation of primer dimer was significantly greater than the delay in the amplification of target. The beneficial effect of the primers is seen comparing target-free reactions with amplifications of template. Using unblocked primers, the number of cycles to reach the AFL occurred about 28 cycles later in amplifications without target. In contrast, using a single reversibly-blocked primer, the number of cycles to reach the AFL occurred about 40 or 31 cycles later, depending on which of the primers was blocked. Using two reversibly-blocked primers, the number of cycles to reach the AFL occurred about 40 cycles later. The results indicate that the use of one or two reversibly blocked primers increased the delay in the formation of template-independent amplification products relative to the amplification of the intended target.

In the present example, amplification of the intended target was clearly distinguishable from template-independent amplification artifacts because of the significant delay in the formation of artifacts. However, in many reactions, the formation of artifacts occurs only a few cycles after amplification of the intended target and can make identification of the intended target problematical. The use of the reversibly blocked primers of the present invention can facilitate clearly identifying the amplification of the intended target by relatively delaying the increase in artifacts.

I claim:

1. A kit for carrying out a nucleic acid amplification reaction, wherein said kit comprises a pair of primers, wherein at least one primer of said pair is reversibly blocked by the covalent attachment of a triarylmethyl group to the 3' terminal OH.

2. A kit of claim 1, wherein said triarylmethyl group has the formula:

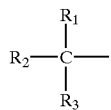

wherein $R_1$, $R_2$, and $R_3$ represent independently an aryl group; a nitrogen, sulfur, or oxygen-containing heterocyclic ring; or an aryl group with a monosubstituent selected from the group consisting of halide, nitro, lower alkyl, lower alkoxy, and aryl, aralkyl, and cycloalkyl containing up to 10 carbon atoms; wherein $R_2$ and $R_3$ each also may be alkyl, aralkyl, or cycloalkyl containing up to 10 carbon atoms.

3. A kit of claim 1, wherein said triarylmethyl group is dimethoxytrityl.

4. A kit of claim 3, wherein both primers of said pair of primers are reversibly blocked.

5. A method for amplifying a nucleic acid target sequence, wherein said method comprises carrying out an amplification reaction using a pair of primers, wherein at least one primer of said pair is reversibly blocked by the covalent attachment of a triarylmethyl group to the 3' terminal OH.

6. A method of claim 5, wherein said triarylmethyl group has the formula:

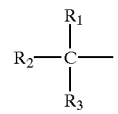

wherein $R_1$, $R_2$, and $R_3$ represent independently an aryl group; a nitrogen, sulfur, or oxygen-containing heterocyclic ring; or an aryl group with a monosubstituent selected from the group consisting of halide, nitro, lower alkyl, lower alkoxy, and aryl, aralkyl, and cycloalkyl containing up to 10 carbon atoms; wherein $R_2$ and $R_3$ each also may be alkyl, aralkyl, or cycloalkyl containing up to 10 carbon atoms.

7. A method of claim 5, wherein said triarylmethyl group is dimethoxytrityl.

8. A method of claim 7, wherein both primers of said pair of primers are reversibly blocked.

* * * * *

SEQUENCE LISTING

<160> NUMBER OF SEQ ID NOS: 4

<210> SEQ ID NO 1
<211> LENGTH: 23
<212> TYPE: DNA
<213> ORGANISM: synthetic construct
<220> FEATURE:
<221> NAME/KEY: misc_feature
<222> LOCATION: ()..()
<223> OTHER INFORMATION: Description of synthetic construct: HIV-1 primer

<400> SEQUENCE: 1
gcatgggtaa aggcagtaga aga                                              23

<210> SEQ ID NO 2
<211> LENGTH: 21
<212> TYPE: DNA
<213> ORGANISM: synthetic construct
<220> FEATURE:
<221> NAME/KEY: misc_feature
<222> LOCATION: ()..()
<223> OTHER INFORMATION: Description of synthetic construct: HIV-1 primer

<400> SEQUENCE: 2
gcatgggtaa aggcagtaga a                                                21

```
<210> SEQ ID NO 3
<211> LENGTH: 23
<212> TYPE: DNA
<213> ORGANISM: synthetic construct
<220> FEATURE:
<221> NAME/KEY: misc_feature
<222> LOCATION: ()..()
<223> OTHER INFORMATION: Description of synthetic construct: HIV-1
      primer

<400> SEQUENCE: 3
ccagcaatgt cacttcctgt tgg                                              23

<210> SEQ ID NO 4
<211> LENGTH: 22
<212> TYPE: DNA
<213> ORGANISM: synthetic construct
<220> FEATURE:
<221> NAME/KEY: misc_feature
<222> LOCATION: ()..()
<223> OTHER INFORMATION: Description of synthetic construct: HIV-1
      primer

<400> SEQUENCE: 4
ccagcaatgt cacttcctgt tg                                               22
```